United States Patent [19]
Ray

[11] Patent Number: 5,527,312
[45] Date of Patent: Jun. 18, 1996

[54] FACET SCREW ANCHOR

[75] Inventor: R. Charles Ray, Tacoma, Wash.

[73] Assignee: Salut, Ltd., Tacoma, Wash.

[21] Appl. No.: 293,222

[22] Filed: Aug. 19, 1994

[51] Int. Cl.⁶ .................................................. A61B 17/70
[52] U.S. Cl. ........................................................ 606/61
[58] Field of Search ................................ 606/60, 61, 69, 606/70, 71

[56] References Cited

U.S. PATENT DOCUMENTS

| 3,824,995 | 7/1974 | Getscher et al. | 606/69 |
| 4,573,458 | 3/1986 | Lower | 606/69 |
| 5,087,259 | 2/1992 | Krenkel | 606/60 |
| 5,318,567 | 6/1994 | Vichard | 606/71 |
| 5,415,661 | 5/1995 | Holmes | 606/69 |

FOREIGN PATENT DOCUMENTS

| 2126903 | 4/1984 | United Kingdom | 606/69 |

OTHER PUBLICATIONS

Friedrich P. Magerl, M.D., "Stabilization of the Lower Thoracic and Lumbar Spine with External Skeletal Fixation," Reprinted from *Clinical Orthopaedics*, vol. 189 (Oct. 1984).

Primary Examiner—Tamara L. Graysay
Attorney, Agent, or Firm—Christensen, O'Connor, Johnson & Kindness

[57] ABSTRACT

A spinal fixation system comprises a pair of facet screws that extend through the facet joint from the inferior facet of a superior vertebra and into the base of the transverse process of the immediately inferior vertebra. A pair of stabilizing bars are operatively coupled to the screws adjacent their heads. The bars carry fingers that extend in a superior direction and loop over the superior aspect of the pedicle of the superior vertebra. The stabilizing bars thus stabilize the facet screws and prevent their tendency to toggle, thereby conjunctively stabilizing the superior vertebra to the immediately inferior vertebra, for example, to facilitate the healing of a fusion.

5 Claims, 2 Drawing Sheets

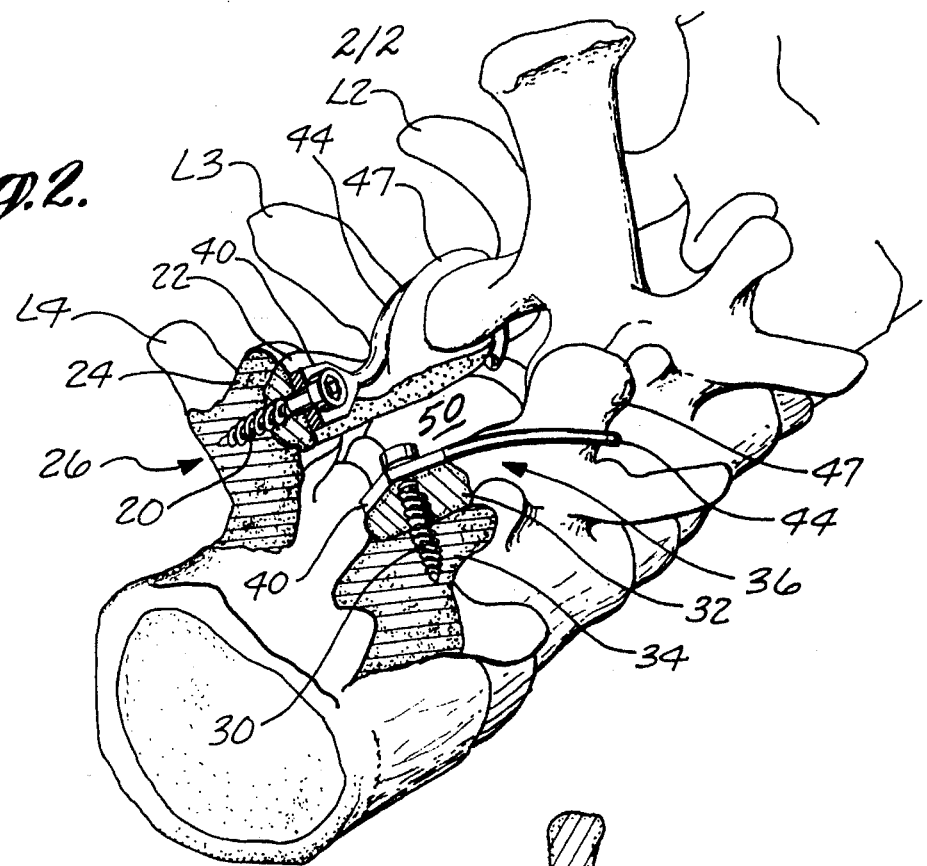
fig.2.
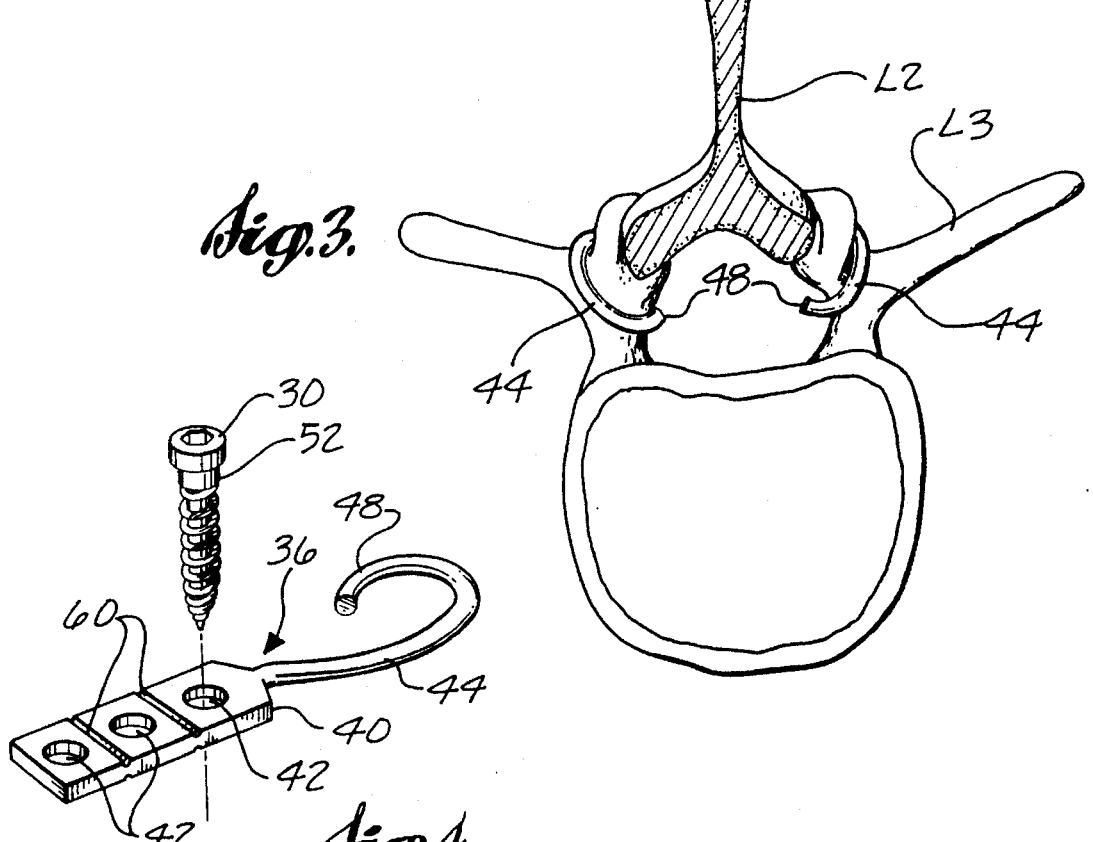
fig.3.
fig.4.

5,527,312

FACET SCREW ANCHOR

FIELD OF THE INVENTION

The present invention relates to surgical devices and methods for reducing deformities of the spine and, more particularly, for fixing two vertebrae relative to each other and holding the same while a fusion of two or more vertebrae heals.

BACKGROUND OF THE INVENTION

Spinal fusions are indicated where a natural spinal deformation has occurred, where there has been damage to intervertebral disks, or where fracture of a vertebra has occurred. One method for fixing vertebrae relative to each other is disclosed in copending patent application Ser. No. 08/075,239, filed Jun. 10, 1993 now U.S. Pat. No. 5,470,333. With the fixation device disclosed therein, one or two plates are secured to the sacrum and a single rod extends from the sacral plates superiorly along the saggital plane posterior to the spine. Transverse bars are rigidly secured to the rod at a location posterior to the vertebra to be fixed. The lateral extensions of these transverse bars are secured bilaterally by screws to the pedicles of the vertebra to be immobilized during the fusion process.

For some deformations and injuries, application of a spinal plate with a superiorly extending rail with transverse bars and pedicle screws are not required. Another method suggested by Magerl for fixation of successive vertebrae is to use translaminar screws. Conventionally, these translaminar screws extend through the spinous process and then through the lamina at the facet joint into and through the pedicle of the successively inferior vertebrae. Oftentimes a deformity and/or injury requires a laminectomy to eliminate nerve root compression, such as occurs with degenerative spondylolisthesis. When a laminectomy is required, the spinous process and the underlying lamina are removed. When the spinous process is removed, translaminar screw fixation is not generally adequate to stabilize successive vertebrae pending healing of the spinal fusion. This is because the lamina of the superior vertebra is generally relatively weak, especially where a laminectomy has been performed. Because the lamina is relatively weak, the translaminar screws can toggle relative to the superior vertebra, causing breakage in the lamina around the screw and destabilization of the joint. Thus, where a laminectomy has been performed, use of a sacral/rod/pedicle fixation system, such as that described above, is normally required.

SUMMARY OF THE INVENTION

The present invention therefor provides a system for stabilizing adjacent vertebra in the thoracolumbar and lumbar regions of the spine, and particularly, for fixing an inferior vertebra to a superior vertebra through the facet joint. The system includes a first facet screw extending through the inferior facet of the superior vertebra lateral to the sagittal plane and extending through the facet joint of the inferior vertebra into the base of the transverse process. A fixation bar is operably secured to the screw so as to prevent toggling of the screw relative to the bar. The bar has a finger that extends in a superior direction across the dorsal side of the transverse process of the superior vertebra. The finger continues by wrapping around the superior aspect of the pedicle of the superior vertebra and extends in an anterior direction, and preferably thereafter in an inferior direction, thus terminating in a hook-like structure that in combination with the screw fixes the structure in position. Preferably, a second screw and fixation bar are applied to the vertebra on the opposite side of the sagittal plane to provide bilateral fixation.

BRIEF DESCRIPTION OF THE DRAWINGS

A better understanding of the present invention can be derived by reading the ensuing specification in conjunction with the accompanying drawings, wherein:

FIG. 2 is an isometric view of the spine and the fixation system of the present invention hooking in a direction that is lateral, superior, and slightly anterior to the spine;

FIG. 3 is a sectional view of the spine and fixation system of the present invention taken along section line 3—3 of FIG. 1; and FIG. 4 is an isometric view of the fixation bar forming a part of the present invention.

DETAILED DESCRIPTION OF THE PREFERRED EMBODIMENT

Figure 1:
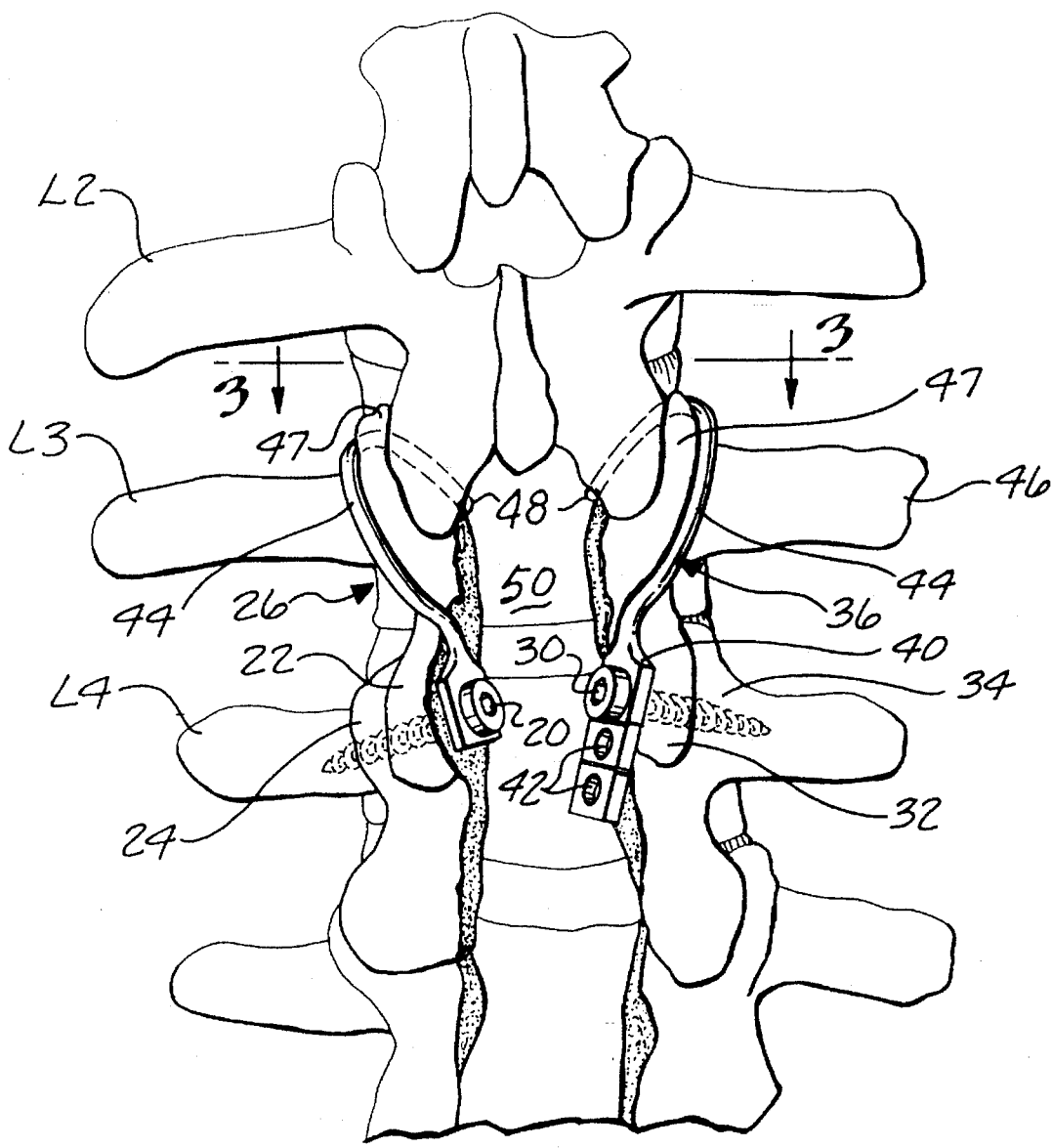
FIG. 1 is a dorsal view of a portion of the lumbar spine and the fixation system of the present invention viewing in an anterior direction.

Referring conjunctively to FIGS. 1, 2 and 3, the present invention is described in relation to fixing the L3 and L4 vertebrae relative to each other. It is understood, however, that the invention is applicable to other vertebrae in the lumbar region, as well as the thoracolumbar junction. As shown, a laminectomy has been performed on the L3 and L4 vertebrae. Thus, the spinous process and the underlying lamina on each side of the sagittal plane have been removed, leaving only the outlying portion of the lamina transverse of the sagittal plane on both the L3 and L4 vertebrae. In accordance with the present invention, a first facet screw 20 is inserted through the lamina 22 of the L3 vertebra in the region of the facet joint on the left side of the sagittal plane. The screw 20 extends in an anterior direction through the facet joint and angles laterally outwardly into the left base of the transverse process 24 of the inferior vertebra L4. A second facet screw 30 extends in an anterior direction through the lamina 32 on the opposite (right) side of the sagittal plane. The screw 30 extends through the facet joint on the right side of the sagittal plane and angles laterally outwardly into the right base of the transverse process 34 of the L4 vertebra. Thus, the screws 20 and 30 diverge in the anterior direction, and are also angled slightly in the inferior direction.

Each of the facet screws 20 and 30 are fitted with a fixation bar, 26 and 36 respectively. The fixation bars 26 and 36 are generally mirror images of each other. The fixation bars will first be described in conjunction with the bar 36 positioned on the right side of the sagittal plane. The fixation bar 36 includes an inferior portion 40 having a plurality of cylindrical bores 42. Each of the bores 42 are generally oriented along parallel axes and spaced in an inferior-superior direction along the inferior bar portion 40. The facet screw extends through one of the bores 42. By choosing the appropriate bore 42 for the facet screw, the relative length of the finger 44 can be varied to provide adjustability for different sized vertebra. The bar 36 has a finger 44 that extends in a superior, and slightly lateral, direction from the inferior portion 40. The finger extends in a superior direction across the dorsal side of the lateral process 46 of L3 and curves in a superior and anterior direction over the superior aspect of the lateral pedicle 47 of L3. The finger then extends in an inferior direction and slightly laterally inwardly before terminating in an anterior end 48 short of the spinal cavity 50. The superior portion of the finger thus forms a hook that extends over and around the L3 pedicle to secure the bar from movement in an inferior direction as well as to prevent rotational movement about the longitudinal axis of the bar. The bar 26 on the left side of the sagittal plane form generally the mirror image of the stabilization bar 36 on the right side of the sagittal plane.

Referring to FIG. 4, a facet screw 30 is shown having a head 54 into which a suitable wrench, such as an Allen wrench, can be inserted to thread it through the facet joint. The portion 52 of the screw 30 adjacent the head is cylindrically shaped. The cylindrical portion 52 has a diameter that is slightly less than the diameter of the bores 42 so as to allow rotational and reciprocal movement of the screw in the bore, but not to allow the screw 30 to toggle relative to its longitudinal axis. Thus, the combination of the finger 44 wrapped around the superior portion of the lateral process 46 and the coaction of the screw holding the inferior portion 40 in place will prevent the toggling of the screw 30 relative to the lamina on the superior vertebra 43.

The inferior portion 40 of the bar 36 also carries a plurality of lateral weakened zones 60 in the form of lateral notches on both surfaces of the inferior portion 40 between each of the bores 42. With the manipulation of the proper tool, one or more sections containing bores 42 can be broken away from the stabilization bar to adjust the length of the inferior portion 40, so that unnecessary portions of the inferior portion can be removed. In FIG. 1, the stabilization bar 26 is shown with the lower two segments of the inferior portion removed.

The combined action of the two facet screws 30 and 20 in conjunction with the stabilization bars 26 and 36 will hold the facet screws rigidly relative to the L3 and L4 vertebrae and prevent toggling of the screws. Thus, even in the absence of a stabilizing bar tying pedicle screws to adjacent vertebrae or to the sacrum, and in the absence of translaminar screws that can extend through the spinous process, two vertebrae, such as L3 and L4, can be stabilized relative to each other pending the healing of a fusion.

The present invention has been described in conjunction with a preferred embodiment. It will be readily understood by one of ordinary skill that the various alterations, substitutions of equivalents, and other changes, can be made without departing from the broad concepts disclosed herein. It is therefore intended that the invention be limited only by the definition contained in the appended claims and equivalents thereof.

The embodiments of the invention in which an exclusive property or privilege is claimed are defined as follows:

1. A system for stabilizing the thoracolumbar and lumbar region of the spine and for fixing an inferior vertebra to a superior vertebra, comprising:

a first facet screw adapted to extend through the inferior facet of the superior vertebra lateral to the sagittal plane and to extend into the base of the transverse process of the inferior vertebra;

a fixation bar operably secured to said screw so as to prevent toggling of the said screw relative to said bar, said bar having a finger configured and arranged to extend in a superior direction across the dorsal side of the transverse process of the superior vertebra, said finger adapted to wrap around the superior aspect of the pedicle of the superior vertebra and extend in an anterior direction and preferably thereafter in an anterior and inferior direction to terminate in a hook.

2. The system of claim 1, further comprising:

a second facet screw adapted to extend through the inferior facet of the superior vertebra on the opposite side of the sagittal plane from the first facet screw and to extend into the base of the transverse process of the inferior vertebra;

a second fixation bar operably secured to said second screw so as to prevent toggling of said second screw relative to said second bar, said second bar having a finger configured and arranged to extend in a superior direction across the dorsal side of the transverse process of the superior vertebra on said opposite side, said finger adapted to wrap around the superior aspect of the pedicle of the superior vertebra on said opposite side and extend in an anterior direction and preferably in an inferior direction to terminate in a second hook.

3. The system of claim 1, wherein said bar has a plurality of adjacent bores through which said facet screw can extend to adjust the length of the finger relative to the screw in a superior direction.

4. The system of claim 3, wherein said bar has weakened portions between each of said bores so that the portion of the bar inferior to the bore through which the facet screw extends can be broken away prior to application.

5. The system of claim 1, wherein said bar has at least one bore through which said screw can extend, said screw having a cylindrical shaft adjacent the head of the screw, said shaft being sized to rotatably and reciprocally fit in said bore and to prevent toggling motion of said screw relative to said bar.

* * * * *